United States Patent
Karram

(10) Patent No.: US 10,105,203 B2
(45) Date of Patent: Oct. 23, 2018

(54) TRANSPERITONEAL PROLAPSE REPAIR SYSTEM AND METHOD

(71) Applicant: Mickey Karram, Cincinnati, OH (US)

(72) Inventor: Mickey Karram, Cincinnati, OH (US)

( * ) Notice: Subject to any disclaimer, the term of this patent is extended or adjusted under 35 U.S.C. 154(b) by 143 days.

(21) Appl. No.: 14/380,373

(22) PCT Filed: Feb. 25, 2013

(86) PCT No.: PCT/US2013/027686
§ 371 (c)(1),
(2) Date: Aug. 22, 2014

(87) PCT Pub. No.: WO2013/126908
PCT Pub. Date: Aug. 29, 2013

(65) Prior Publication Data
US 2015/0025309 A1    Jan. 22, 2015

Related U.S. Application Data

(60) Provisional application No. 61/602,288, filed on Feb. 23, 2012.

(51) Int. Cl.
*A61F 2/00* (2006.01)
*A61B 17/06* (2006.01)
(Continued)

(52) U.S. Cl.
CPC ............ *A61F 2/0022* (2013.01); *A61B 17/02* (2013.01); *A61B 17/0401* (2013.01);
(Continued)

(58) Field of Classification Search
CPC ............ A61B 17/0401; A61B 17/0483; A61B 2017/00557; A61B 2017/00805;
(Continued)

(56) References Cited

U.S. PATENT DOCUMENTS

| | | | | |
|---|---|---|---|---|
| 2008/0249534 A1* | 10/2008 | Gruber | ............ | A61B 1/303 606/119 |
| 2009/0023982 A1* | 1/2009 | Karram | ............ | A61B 17/0401 600/37 |

(Continued)

FOREIGN PATENT DOCUMENTS

| | | | | |
|---|---|---|---|---|
| WO | WO 2010028242 A1 * | 3/2010 | ............ | A61F 2/0045 |
| WO | WO 2011082350 A1 * | 7/2011 | ....... | A61F 17/00234 |

OTHER PUBLICATIONS

Karram, Mikey, and Christine Vaccaro. "High Uterosacral Vaginal Vault Suspension to Repair Enterocele and Apical Prolapse." OBG Management 23.6 (Jun. 2011): 34-43. Web. Apr. 12, 2016.*

(Continued)

*Primary Examiner* — Christine H Matthews

(57) ABSTRACT

A prolapse repair system and procedure are provided. The system can include one or more anchor devices and one or more extending members, such as a suture. The system can further include a mesh or like support or suspension structure provided intermediate the one or more anchor devices and the one or more extending members. The anchors can be directed to the coccygeous sacrospinous ligament or complex via a transperitoneal approach, wherein the one or more anchor devices are engaged directly into the target ligament or tissue complex and the one or more sutures extend back through the thickness of the vaginal wall to provide vaginal wall support.

18 Claims, 5 Drawing Sheets

(51) Int. Cl.
  *A61B 17/00* (2006.01)
  *A61B 17/02* (2006.01)
  *A61B 17/04* (2006.01)

(52) U.S. Cl.
  CPC .... *A61B 17/06109* (2013.01); *A61B 17/0483* (2013.01); *A61B 2017/00557* (2013.01); *A61B 2017/00805* (2013.01); *A61B 2017/0225* (2013.01); *A61B 2017/0409* (2013.01); *A61B 2017/0412* (2013.01); *A61B 2017/0417* (2013.01); *A61B 2017/0427* (2013.01); *A61B 2017/0437* (2013.01); *A61B 2017/0464* (2013.01); *A61F 2/0045* (2013.01); *A61F 2210/0004* (2013.01); *A61F 2220/0008* (2013.01)

(58) Field of Classification Search
  CPC .... A61B 2017/0225; A61B 2017/0409; A61B 2017/0412; A61B 2017/0417; A61B 2017/0427; A61B 2017/0437; A61B 2017/0464; A61B 17/00234; A61F 2210/0004; A61F 2220/00; A61F 2/0004–2/0045; A61F 2/0063; A61F 2220/0016; A61F 2220/0008; A61F 2/0036; A61F 2/0009; A61F 2/0022; A61F 2250/0031; A61F 2/004
  See application file for complete search history.

(56) References Cited

U.S. PATENT DOCUMENTS

| | | | | |
|---|---|---|---|---|
| 2010/0261954 | A1* | 10/2010 | Townsend | A61F 2/0045 600/37 |
| 2011/0082331 | A1* | 4/2011 | Montpetit | A61B 17/0401 600/37 |
| 2011/0105836 | A1* | 5/2011 | Miller | A61F 2/0045 600/37 |
| 2011/0263930 | A1* | 10/2011 | Rapp | A61F 2/0045 600/37 |

OTHER PUBLICATIONS

First Examiner's Report of Australian Application No. 2016277767, dated Mar. 19, 2018, 2 pages.

* cited by examiner

TRANSPERITONEAL PROLAPSE REPAIR SYSTEM AND METHOD

CROSS-REFERENCE TO RELATED APPLICATIONS

This Application is a national stage application filed under 35 U.S.C. § 371 of International Application No. PCT/US2013/027686, filed Feb. 25, 2013, which claims priority to and the benefit of U.S. Provisional Patent Application No. 61/602,288, filed Feb. 23, 2012, both of which are incorporated herein by reference in their entirety.

FIELD OF THE INVENTION

The present invention relates generally to surgical methods and apparatus and, more specifically, to systems and methods of treating pelvic conditions, such as urinary or fecal incontinence and female vaginal prolapse conditions, including enterocele, rectocele or posterior prolapse.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor via a transperitoneal procedure.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Posterior prolapse, or rectocele, can occur when the fascia that separates the rectum and the vagina weakens or tears, thereby causing a bulge of the vaginal wall. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

Urinary incontinence can be characterized by the loss or diminution in the ability to maintain the urethral sphincter closed as the bladder fills with urine. Male or female stress urinary incontinence (SUI) occurs when the patient is physically stressed.

A variety of treatment options are currently available to treat incontinence. Some of these treatment options include external devices, behavioral therapy (such as biofeedback, electrical stimulation, or Kegal exercises), injectable materials, prosthetic devices and/or surgery. Depending on age, medical condition, and personal preference, surgical procedures can be used to completely restore continence. Types of procedure found to be an especially successful treatment option for SUI in both men and women can include sling or implant procedures. There are a variety of different sling procedures. Slings used for pubovaginal procedures differ in the type of material and anchoring methods.

One such implant procedure is the Elevate® anterior or posterior implant systems sold by American Medical Systems, Inc. of Minnetonka, Minn. The Elevate® posterior implant system utilizes self-fixating tips that allow for mesh placement in the sacrospinous ligament through a single vaginal incision to treat apical and/or posterior vaginal prolapse.

There is a desire to provide a system for repairing apical support and posterior vaginal wall support based on sound anatomic concepts and long term outcome advantages.

SUMMARY OF THE INVENTION

The present invention provides prolapse repair system and procedure for treating incontinence and prolapse by repairing vaginal apical support and posterior vaginal wall support. The system can include one or more anchor devices and one or more extending members, such as a suture. The system can further include a mesh or like support or suspension structure provided intermediate the one or more anchor devices and the one or more extending members.

To facilitate the repairs, anchoring can be directed to the coccygeous sacrospinous ligament or complex, or other like anatomical structures, via a transperitoneal (through the peritoneum) approach, wherein the one or more anchor devices are engaged directly into the target ligament or tissue complex. The one or more extending suture members can be constructed of an absorbable, or continuous delayed absorbable, material. With such a transperitoneal approach, improved bilateral suspension can be achieved with less deviation of the vaginal axis resulting.

A vaginal retractor can be employed to keep the small bowel from dropping into the field, as well as to provide adequate lighting and displacement of the sigmoid colon. The retractor can include an inflation member or device (e.g., via fluid inflation internal or external to the retractor) that upon intraperitoneal insertion can occupy the upper pelvis to lift the intestinal contents out of the pelvis.

DETAILED DESCRIPTION OF PREFERRED EMBODIMENTS

Figure 1:
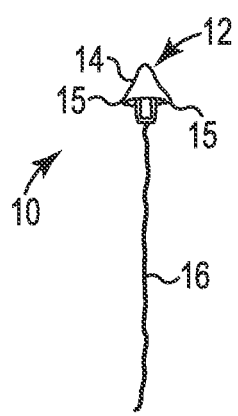
FIGS. 1-2 are views of anchor devices having one or more extending suture members, in accordance with embodiments of the present invention.
Figure 2:
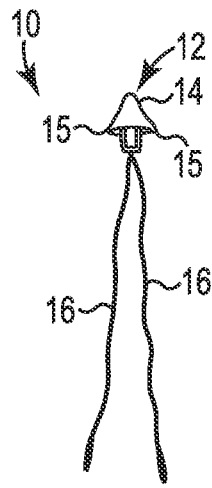
Figure 3:
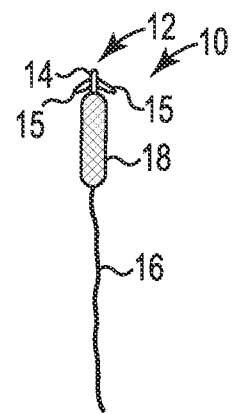
FIGS. 3-4 are views of anchor devices having a mesh portion and one or more extending suture members, in accordance with embodiments of the present invention.
Figure 4:
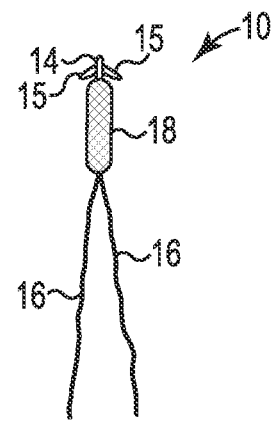
Figure 5:
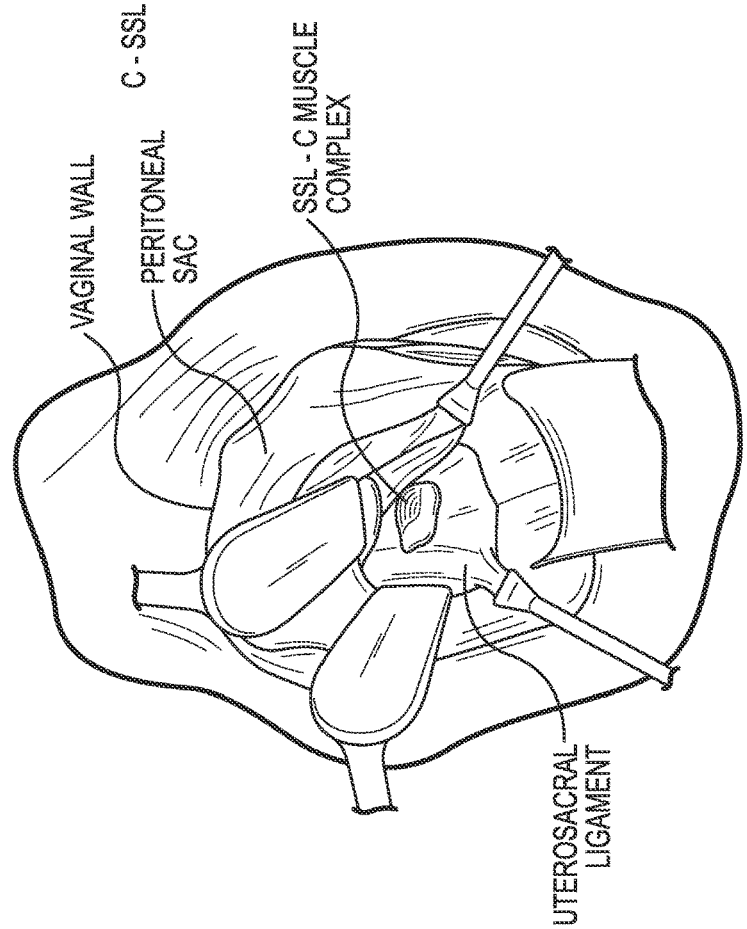
FIG. 5 is a schematic anatomical view showing access to the target tissue sites for a transperitoneal approach, in accordance with embodiments of the present invention.
Figure 6:
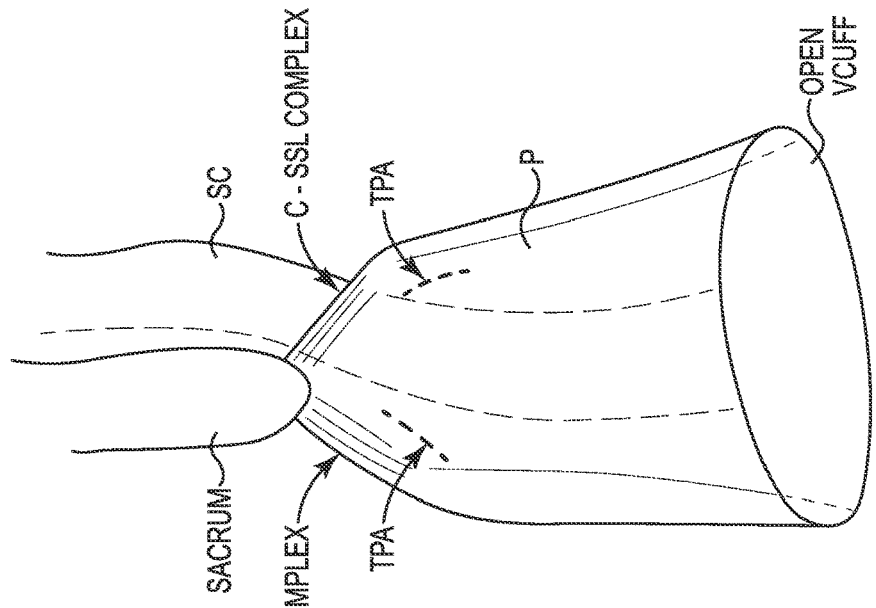
FIG. 6 is a schematic anatomical view of transperitoneal access to the C-SSL complex by making a window in the peritoneum, in accordance with embodiments of the present invention.

Referring generally to FIGS. 1-12, a prolapse repair system 10 and methods are shown. Various embodiments of the system 10 can include anchor support devices 12 having one or more anchors 14 and one or more members 16 extending from the one or more anchors 14. The one or more anchors can include angled tines 15 to promote engagement and fixation within tissue of the patient. The one or more members 16 can be a suture member. The suture members 16 can be constructed of a material adapted to absorb into the body over time (e.g., continuous delayed absorption). In certain embodiments, the one or more members 16 can include two or more suture members extending from the anchor, as shown in FIGS. 2 and 4. The anchor 14 can be constructed of a polymer or like material. The system 10 provides a device and procedure that can position the vaginal apex so that it is not distorted, or at least reduces any distortion.

Various embodiments of the anchor support device 12 can include a mesh portion or member 18 provided intermediate the anchor 14 and the one or member 16s, as shown in FIGS. 3-4. As such, the mesh member 18 can support or reinforce tissue upon deployment. The mesh member 18 can be constructed of polymer filament materials, or can be molded or otherwise formed into a generally planar structure or from a thin generally planar film or sheet material. Examples of acceptable polymer materials available in constructing or forming portions of the anchor device 12 and its components can include polypropylene, polyethylene, fluoropolymers, metals or like materials. The various implants or systems, anchors, mesh, tools, devices, features and methods disclosed in U.S. Patent Application Publication No. 2011/0112357 are envisioned, in whole or in part, for use with embodiments of the present invention. Accordingly, the above-identified publication is fully incorporated herein by reference in its entirety.

The anchor support device 12 can be deployed and provided to repair vaginal apical support and posterior vaginal wall support via a transperitoneal (through the peritoneum P) approach. Namely, the physician can access the coccygeous muscle-sacrospinous ligament complex (C-SSL complex), or the sacrospinous ligament, via a transperitoneal access approach TPA (e.g., FIG. 6, via small peritoneum P window or opening(s)) and insert one or more of the anchors 14 directly into the target ligament, on each side of the patient, with the suture members 16 extending from the anchors 14 to serve as suspension members to the vaginal wall. A transperitoneal access approach allows for easy bilateral suspension with less deviation of the vaginal axis and provides an advantageous route for the procedure.

Figure 12:
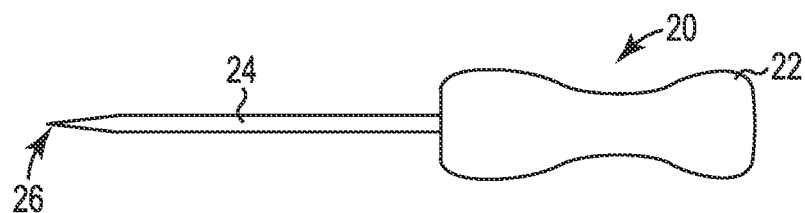
FIG. 12 is an anchor deployment tool, in accordance with embodiments of the present invention.

A needle device 20, as shown in FIG. 12, can be included with the system 10 to deploy and fixate the anchors 14 at the target site. The needle device 20 can include a handle portion 22 and a needle portion 24. The needle portion 24 can be straight or curved and a distal tip 26 is adapted to selectively engage and disengage with the anchors 14. The tip of the anchors 14 and/or the distal 26 of the needle device 20 can facilitate passing the anchors 14 and the attached members 14 through (e.g., pushing through) a tissue pathway, tissue, and eventually the target tissue site. One or more actuators or like mechanisms can be included to facilitate the release or disengagement of the anchor 14 from the distal tip 26.

Figure 7:
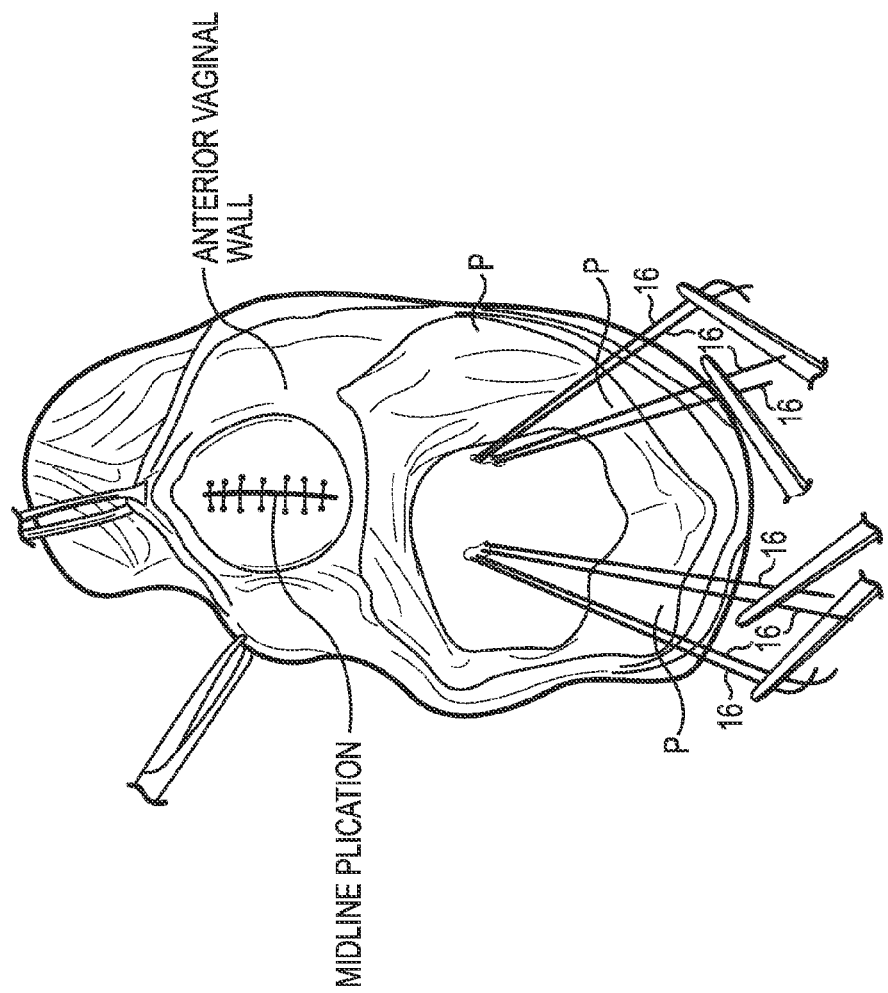
FIGS. 7-8 are schematic anatomical views of a plurality of suture members extending out through the vaginal wall after transperitoneal deployment of anchor devices, in accordance with embodiments of the present invention.
Figure 8:
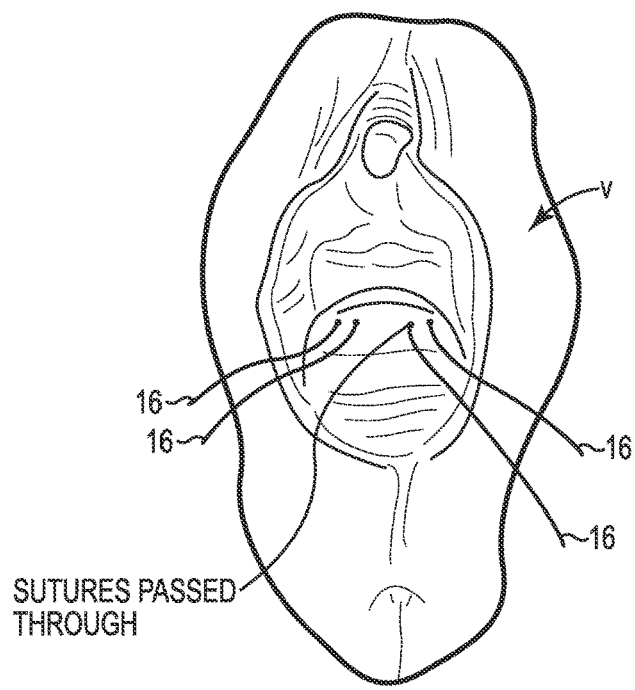
Figure 9:
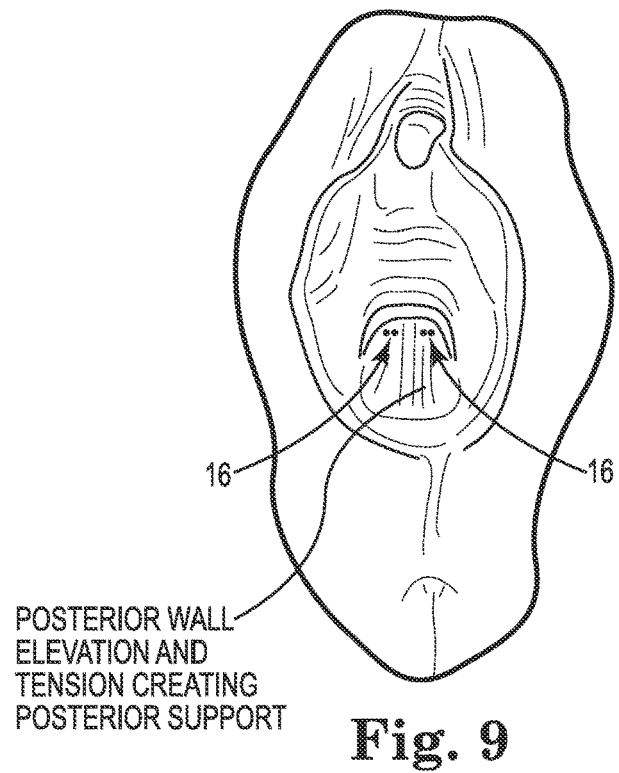
FIG. 9 is a schematic anatomical view of suture members cut and tied off to create tension and create support and posterior vaginal wall elevation, in accordance with embodiments of the present invention.
Figure 10:
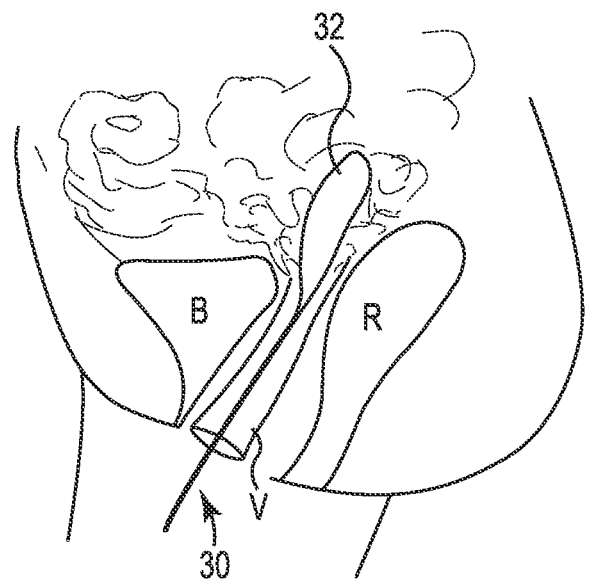
FIG. 10 is a schematic anatomical view of a retractor device having an inflation member deployed to keep the small bowel from dropping into the procedure field, in accordance with embodiments of the present invention.

Once the anchors 14 are engaged with the target tissue site, the suspension sutures 16 are brought out through the full thickness of the posterior vaginal wall (e.g., including the peritoneum P), as demonstrated in FIG. 7-9. As depicted in FIG. 7, two anchors 14 can be fixated in the target ligament site on each side of the patient, thereby providing four suspension sutures 16 extending through the posterior vaginal wall on each side (e.g., total of eight). Other embodiments can use a single anchor 14 on each side, or three or more anchors on each side, depending on the repair needs and the anatomical structure of the patient. The suspension sutures 16 can be tied together (e.g., to another adjacent suture) for tensioning, thereby recreating level 3 support and facilitating posterior wall support and correction of the high rectocele (FIG. 9). In other embodiments, the anchor 14 can be passed with the suture members 16 directly into the upper portion of the uterosacral ligament in lieu of or in addition to another target site such as the C-SSL complex.

Figure 11:
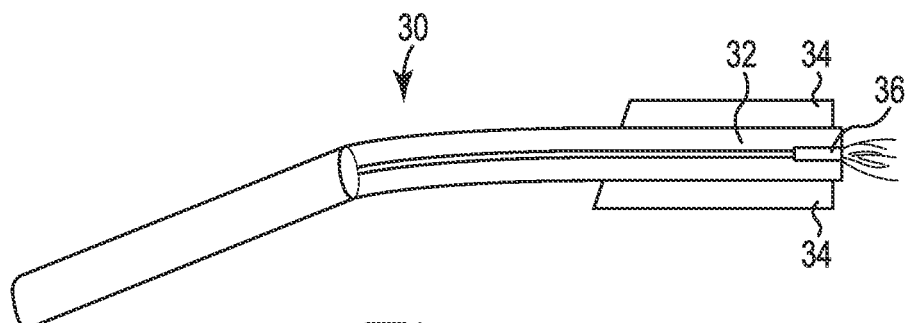
FIG. 11 is a schematic view of a retractor device having an illumination feature, in accordance with embodiments of the present invention.

It can be a challenge to obtain adequate exposure to all safe passages of the anchors 14 and sutures 16 in the respective ligaments (uterosacral or sacrospinous) with a intraperitoneal suspension as is disclosed herein. However, a vaginal retractor 30 can be employed (e.g., through the vagina V) to keep the small bowel from dropping into the field, as well as to provide adequate lighting and displacement of the sigmoid colon, as demonstrated in FIG. 10. The retractor 30 can include an inflation member or device 32 (e.g., via fluid (gas or liquid) inflation internal or external to the retractor 30) that upon intraperitoneal insertion can occupy the upper pelvis to lift the intestinal contents out of the pelvis. As shown in FIG. 11, the end of the retractor 30 including the device 32 can include firm but generally flexible extensions 34 provided and positioned on the retractor 30 to prevent bowel from slipping down around the balloon device 32 during use. The long, generally flat retractor 30 can include an illumination device 36 to promote visualization in the field during deployment and use.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. A transperitoneal prolapse repair system, comprising:
a first support device and a second support device, each of the first support device and the second support device having an anchor and one or more members extending from the anchor, the anchor having tines to engage target tissue, the anchor being adapted to be deployed through a peritoneum opening and fixated in the coccygeus muscle-sacrospinous ligament complex and the one or more members being adapted to be directed back through a portion of a vaginal wall such that the first support device provides posterior elevation on a first side of the vaginal wall and the second support device provides posterior elevation on a second side of the vaginal wall;
a needle device including a distal tip adapted to selectively engage with the anchor of at least the first support device to selectively push the anchor of at least the first support device through target tissue; and a retractor having a proximal end portion and a distal end portion, the distal end portion of the retractor having an inflatable member configured to lift a bowel from a procedure pathway, the retractor having a first flexible extension extending from a first side of the distal end portion of the retractor, and a second flexible extension extending from a second side of the distal end portion of the retractor, the first side being opposite the second side, the first flexible extension and the second flexible extension being planar and extending in opposite directions, the first flexible extension and the second flexible extension configured to prevent the bowel from slipping down around the inflatable member during use.

2. The system of claim 1, wherein the one or more members extending from the anchor are suture members.

3. The system of claim 2, wherein the suture members are absorbable.

4. The system of claim 3, wherein the absorbable suture members are continuous delayed absorbable suture members.

5. The system of claim 1, wherein the one or more members includes two or more suture members.

6. The system of claim 1, further including a second anchor having one or more members extending from the second anchor.

7. The system of claim 6, wherein the one or more members of the second anchor includes two or more suture members.

8. The system of claim 1, wherein at least the first support device further includes a support member provided intermediate the respective anchor and the one or more extending members.

9. The system of claim 8, wherein the support member is a mesh support member.

10. The system of claim 1, wherein the retractor further includes an illumination device.

11. A transperitoneal prolapse repair system, comprising:
a first support device having a first anchor and a pair of suspension sutures extending from the first anchor such that the first anchor is adapted to engage a sacrospinous ligament site at a first side of a patient, wherein the pair of sutures of the first support device are adapted to extend back through a portion of a peritoneum to provide vaginal wall support on a first vaginal wall side;
a second support device having a second anchor and a pair of suspension sutures extending from the second anchor such that the second anchor is adapted to engage a sacrospinous ligament site on a second side of the patient, wherein the pair of sutures of the second support device are adapted to extend back through a portion of a peritoneum to provide vaginal wall support on a second vaginal wall side separate from the first vaginal wall side;
a needle device including a distal tip adapted to selectively engage with at least the first anchor to selectively push the first anchor through target tissue; and
a retractor having a proximal end portion and a distal end portion, the distal end portion of the retractor having an inflatable member configured to lift a bowel from a procedure pathway, the retractor having a first flexible extension extending from a first side of the distal end portion of the retractor, and a second flexible extension extending from a second side of the distal end portion of the retractor, the first side being opposite the second side, the first flexible extension and the second flexible extension configured to prevent the bowel from slipping down around the inflatable member during use, the first flexible extension and the second flexible extension being planar and extending in opposite directions.

12. The system of claim 11, wherein the pair of suspension sutures of the first and second support devices are absorbable.

13. The system of claim 12, wherein the absorbable suspension sutures are continuous delayed absorbable suspension sutures.

14. The system of claim 11, wherein the first support device further includes a support member provided intermediate the first anchor and the pair of suspension sutures of the first support device.

15. The system of claim 14, wherein the support member is a mesh support member.

16. The system of claim 11, wherein the second support device further includes a support member provided intermediate the second anchor and the pair of suspension sutures of the second support device.

17. The system of claim 16, wherein the support member is a mesh support member.

18. The system of claim 11, wherein the retractor further includes an illumination device.

\* \* \* \* \*